(12) United States Patent
Sanders

(10) Patent No.: US 7,655,597 B1
(45) Date of Patent: Feb. 2, 2010

(54) PESTICIDE COMPOSITIONS INCLUDING POLYMERIC ADJUVANTS

(75) Inventor: John Larry Sanders, Leawood, KS (US)

(73) Assignee: Specialty Fertilizer Products, LLC, Leawood, KS (US)

(*) Notice: Subject to any disclaimer, the term of this patent is extended or adjusted under 35 U.S.C. 154(b) by 0 days.

(21) Appl. No.: 12/534,481

(22) Filed: Aug. 3, 2009

(51) Int. Cl.
*A01N 25/00* (2006.01)
*A01N 57/26* (2006.01)
*A01N 25/28* (2006.01)

(52) U.S. Cl. .................... 504/116.1; 504/206; 504/360; 504/361

(58) Field of Classification Search ............... 424/406, 424/407, 408, 409; 504/116.1, 189, 206, 504/207, 326, 360, 361
See application file for complete search history.

(56) References Cited

U.S. PATENT DOCUMENTS

| | | | |
|---|---|---|---|
| 4,557,929 A | 12/1985 | Wysong | |
| 4,867,972 A | 9/1989 | Girardeau et al. | |
| 6,093,679 A | 7/2000 | Azuma et al. | |
| 6,146,652 A | 11/2000 | Gore et al. | |
| 6,515,091 B2 | 2/2003 | Sanders et al. | |
| 6,610,282 B1 | 8/2003 | Ghosh | |
| 6,677,399 B2 | 1/2004 | Herbert et al. | |
| 6,703,469 B2 | 3/2004 | Sanders et al. | |
| 6,706,666 B2 | 3/2004 | Hasebe et al. | |
| 6,897,184 B2 | 5/2005 | Kurita et al. | |
| 7,407,667 B2 | 8/2008 | Zerrer et al. | |
| 2004/0226331 A1 | 11/2004 | Sanders et al. | |
| 2004/0248741 A1 | 12/2004 | Gotsche et al. | |
| 2005/0090402 A1* | 4/2005 | Dieing et al. | ............... 504/361 |
| 2008/0167189 A1 | 7/2008 | Oetter et al. | |
| 2008/0171658 A1 | 7/2008 | Dyllick-Brenzinger et al. | |

* cited by examiner

*Primary Examiner*—Johann R Richter
*Assistant Examiner*—Andriae M Holt
(74) *Attorney, Agent, or Firm*—Hovey Williams LLP

(57) ABSTRACT

Pesticidal compositions of improved effectiveness are provided, including a pesticide (e.g., an insecticide or herbicide) together with a copolymer adjuvant or additive selected from the group consisting of acid or salt copolymers containing individual quantities of maleic and itaconic moieties. The compositions of the invention provide multiple-fold increases in effectiveness, as compared with an equal amount of the pesticide in the absence of the copolymer.

18 Claims, No Drawings

PESTICIDE COMPOSITIONS INCLUDING POLYMERIC ADJUVANTS

BACKGROUND OF THE INVENTION

1. Field of the Invention

The present invention is broadly concerned with pesticide compositions and methods wherein the compositions include a broad class of pesticides, especially insecticides and herbicides and mixtures thereof, together with an amount of a copolymer adjuvant or additive serving to significantly increase the effectiveness of the pesticide. More particularly, the invention is concerned with such compositions and methods wherein a copolymer including respective quantities of maleic and itaconic moieties is mixed or used with a selected pesticide.

2. Description of the Prior Art

The chemistries of pesticides, and especially insecticides and herbicides, are diverse and well known. Large numbers of such pesticides have been developed in the past, some of which are broad spectrum (e.g., glyphosate) while others have more specific utilities (e.g., triazine for corn). In all instances, however, efforts are made to minimize the use of pesticide to obtain the same or enhanced effectiveness. This is done for reasons of cost and also to minimize the environmental impact of pesticidal usage.

A wide variety of adjuvants and additives have been used in the past with pesticidal formulations. These include pH modifiers, surfactants, anti-foam agents, anti-evaporants, buffers, penetrating agents, compatibility agents, defoamers, deposition agents, drift-control agents with sprays, extenders, foaming agents, humectants, spreaders, stickers, wetting agents, and water conditioners. While these expedients are known to marginally increase pesticide performance, in general they do not provide significant, multiple-fold increases in pesticidal effectiveness.

There is accordingly a real and unsatisfied need in the art for a class of adjuvants or additives which can very significantly increase the effectiveness of pesticides without themselves posing excessive cost or environmental impact problems.

SUMMARY OF THE INVENTION

The present invention overcomes the problems outlined above and provides pesticide compositions comprising respective quantities of a pesticide and a copolymer containing individual quantities of maleic and itaconic moieties. The pesticide component can be any agent with pesticidal activity (e.g., herbicides, insecticides, fungicides, and nematocides) and is preferably selected from the group consisting of insecticides, herbicides, and mixtures thereof. The well known pyrethroid and organophosphate pesticides are suitable for use in the invention, as well as glyphosate herbicides.

The preferred copolymer adjuvants of the invention are the copolymers containing maleic and itaconic moieties, usually derived from the corresponding acids or anhydrides. While other monomers may also be used in the maleic-itaconic copolymers, it is preferred that these be present only in minor amounts of up to about 7% by weight, more preferably up to about 4% by weight. Stated otherwise, the copolymers should comprise at least about 93% by weight, more preferably about 96% by weight, of itaconic and maleic monomers. Most preferably, the copolymer consists essentially of or is entirely made up of maleic and itaconic moieties. Furthermore, while other polymers or copolymers can form a part of the compositions of the invention, in preferred aspects, the itaconic/ maleic copolymers are the preponderant polymer fraction in the compositions. Generally, the compositions include respective pesticide and polymeric fractions, with the polymeric fraction having at least about 60% by weight (more preferably at least about 80% by weight, and most preferably at least about 90% by weight) of the preferred itaconic/maleic copolymers, where the total weight of the polymer fraction is taken as 100% by weight. Most preferably, the polymer fraction consists essentially of the itaconic/maleic copolymers, i.e., it is essentially free of other types of monomers.

The compositions of the invention can be used in essentially any context where pesticidal properties are necessary or desirable, e.g., in agricultural uses for soil or foliar applications, or onto hard surfaces such as in home or building pest control. Likewise, the compositions may be applied by any known means as liquids or solids. In agricultural applications, the compositions are preferably aqueous dispersions or solutions, suitable for broadcast spray application. Generally, the compositions of the invention provide at least about a two-fold, and more preferably about a three-fold, greater pesticidal effectiveness, as compared with an equal amount of the pesticide in the absence of the copolymer adjuvant or additive hereof.

DETAILED DESCRIPTION OF THE PREFERRED EMBODIMENTS

The present invention is predicated upon the discovery that the effectiveness of a wide spectrum of pesticides can be significantly improved by a copolymeric adjuvant or additive. Most desirably, the copolymer is blended with the pesticide to form a mixture which then can be applied to soil, in foliar applications, onto hard surfaces, as aerosols, as additives to liquid or solid compositions (e.g., manure), or in any other context where pesticidal activity is desired. Alternately, the pesticide and copolymer may be simultaneously or sequentially (typically within 24 hours of each other) applied to soil. Where mixed compositions are employed, they are typically in the form of aqueous dispersions or solutions, generally having water, pesticide, and copolymer fractions. Other minor ingredients may also be used in the compositions such as surfactants and pH adjustment agents, or any of the other aforementioned adjuvants or additives known in the art.

The pesticides used in the compositions of the invention are broadly selected from insecticides and herbicides. In the context of insecticides, synthetic pyrethroids and organophosphates are particularly preferred. For example, permethrin ($C_{21}H_{20}C_{12}O_3$, (3-phenoxyphenyl)methyl 3-(2,2-dichloroethenyl)-2,2-dimethyl-cyclopropane-1-carboxylate, CAS#52645-53-1) and bifenthrin ($C_{23}H_{22}ClF_3O_2$, (2-methyl-3-phenylphenyl)methyl (1S,3S)-3-[(Z)-2-chloro-3,3,3-trifluoroprop-1-enyl]-2,2-dimethylcyclopropane-1-carboxylate, CAS#82657-04-3) are suitable pyrethroids. A typical organophosphate pesticide useful in the invention is malathion ($C_{10}H_{19}O_6PS_2$,2-(dimethoxyphosphinothioylthio) butanedioic acid diethyl ester, CAS#121-75-5).

More generally, the following insecticides are useful in the invention:

antibiotic insecticides: allosamidin, thuringiensin
    macrocyclic lactone insecticides
        avermectin insecticides: abamectin, doramectin, emamectin, eprinomectin, ivermectin, selamectin
        milbemycin insecticides: lepimectin, ilbemectin, milbemycin oxime, moxidectin
        spinosyn insecticides: spinetoram, spinosad arsenical insecticides: calcium arsenate, copper acetoarsenite, copper arsenate, lead arsenate, potassium arsenite, sodium arsenite botanical insecticides: anabasine, azadirachtin, d-limonene, nicotine, pyrethrins (cinerins (cinerin I, cinerin II), jasmolin I, jasmolin II, pyrethrin I, pyrethrin II), quassia, rotenone, ryania, sabadilla carbamate insecticides: bendiocarb, carbaryl
- benzofuranyl methylcarbamate insecticides: benfuracarb, carbofuran, carbosulfan, decarbofuran, furathiocarb
- dimethylcarbamate insecticides: dimetan, dimetilan, hyquincarb, pirimicarb
- oxime carbamate insecticides: alanycarb, aldicarb, aldoxycarb, butocarboxim, butoxycarboxim, methomyl, nitrilacarb, oxamyl, tazimcarb, thiocarboxime, thiodicarb, thiofanox
- phenyl methylcarbamate insecticides: allyxycarb, aminocarb, bufencarb, butacarb, carbanolate, cloethocarb, dicresyl, dioxacarb, EMPC, ethiofencarb, fenethacarb, fenobucarb, isoprocarb, methiocarb, metolcarb, mexacarbate, promacyl, promecarb, propoxur, trimethacarb, XMC, xylylcarb desiccant insecticides: boric acid, diatomaceous earth, silica gel diamide insecticides: chlorantraniliprole, cyantraniliprole, flubendiamide dinitrophenol insecticides: dinex, dinoprop, dinosam, DNOC fluorine insecticides: barium hexafluorosilicate, cryolite, sodium fluoride, sodium hexafluorosilicate, sulfluramid formamidine insecticides: amitraz, chlordimeform, formetanate, formparanate fumigant insecticides: acrylonitrile, carbon disulfide, carbon tetrachloride, chloroform, chloropicrin, para-dichlorobenzene, 1,2-dichloropropane, ethyl formate, ethylene dibromide, ethylene dichloride, ethylene oxide, hydrogen cyanide, iodomethane, methyl bromide, methylchloroform, methylene chloride, naphthalene, phosphine, sulfuryl fluoride, tetrachloroethane inorganic insecticides: borax, boric acid, calcium polysulfide, copper oleate, diatomaceous earth, mercurous chloride, potassium thiocyanate, silica gel, sodium thiocyanate, see also arsenical insecticides, see also fluorine insecticides insect growth regulators
- chitin synthesis inhibitors: bistrifluron, buprofezin, chlorfluazuron, cyromazine, diflubenzuron, flucycloxuron, flufenoxuron, hexaflumuron, lufenuron, novaluron, noviflumuron, penfluoron, teflubenzuron, triflumuron
- juvenile hormone mimics: epofenonane, fenoxycarb, hydroprene, kinoprene, methoprene, pyriproxyfen, triprene
- juvenile hormones: juvenile hormone I, juvenile hormone II, juvenile hormone III
- moulting hormone agonists: chromafenozide, halofenozide, methoxyfenozide, tebufenozide
- moulting hormones: a-ecdysone, ecdysterone
- moulting inhibitors: diofenolan
- precocenes: precocene I, precocene II, precocene III
- unclassified insect growth regulators: dicyclanil nereistoxin analogue insecticides: bensultap, cartap, thiocyclam, thiosultap nicotinoid insecticides: flonicamid
- nitroguanidine insecticides: clothianidin, dinotefuran, imidacloprid, thiamethoxam
- nitromethylene insecticides: nitenpyram, nithiazine
- pyridylmethylamine insecticides: acetamiprid, imidacloprid, nitenpyram, thiacloprid organochlorine insecticides: bromo-DDT, camphechlor, DDT (pp'-DDT), ethyl-DDD, HCH (gamma-HCH, lindane), methoxychlor, pentachlorophenol, TDE
- cyclodiene insecticides: aldrin, bromocyclen, chlorbicyclen, chlordane, chlordecone, dieldrin, dilor, endosulfan (alpha-endosulfan), endrin, HEOD, heptachlor, HHDN, isobenzan, isodrin, kelevan, mirex organophosphorus insecticides
- organophosphate insecticides: bromfenvinfos, chlorfenvinphos, crotoxyphos, dichlorvos, dicrotophos, dimethylvinphos, fospirate, heptenophos, methocrotophos, mevinphos, monocrotophos, naled, naftalofos, phosphamidon, propaphos, TEPP, tetrachlorvinphos
- organothiophosphate insecticides: dioxabenzofos, fosmethilan, phenthoate
  - aliphatic organothiophosphate insecticides: acethion, amiton, cadusafos, chlorethoxyfos, chlormephos, demephion (demephion-O, demephion-S), demeton (demeton-O, demeton-S), demeton-methyl (demeton-O-methyl, demeton-S-methyl), demeton-S-methylsulphon, disulfoton, ethion, ethoprophos, IPSP, isothioate, malathion, methacrifos, oxydemeton-methyl, oxydeprofos, oxydisulfoton, phorate, sulfotep, terbufos, thiometon
  - aliphatic amide organothiophosphate insecticides: amidithion, cyanthoate, dimethoate, ethoate-methyl, formothion, mecarbam, omethoate, prothoate, sophamide, vamidothion
  - oxime organothiophosphate insecticides: chlorphoxim, phoxim, phoxim-methyl
  - heterocyclic organothiophosphate insecticides: azamethiphos, coumaphos, coumithoate, dioxathion, endothion, menazon, morphothion, phosalone, pyraclofos, pyridaphenthion, quinothion
  - benzothiopyran organothiophosphate insecticides: dithicrofos, thicrofos
  - benzotriazine organothiophosphate insecticides: azinphos-ethyl, azinphos-methyl
  - isoindole organothiophosphate insecticides: dialifos, phosmet
  - isoxazole organothiophosphate insecticides: isoxathion, zolaprofos
  - pyrazolopyrimidine organothiophosphate insecticides: chlorprazophos, pyrazophos
  - pyridine organothiophosphate insecticides: chlorpyrifos, chlorpyrifos-methyl
  - pyrimidine organothiophosphate insecticides: butathiofos, diazinon, etrimfos, lirimfos, pirimiphos-ethyl, pirimiphos-methyl, primidophos, pyrimitate, tebupirimfos
  - quinoxaline organothiophosphate insecticides: quinalphos, quinalphos-methyl
  - thiadiazole organothiophosphate insecticides: athidathion, lythidathion, methidathion, prothidathion
  - triazole organothiophosphate insecticides: isazofos, triazophos
  - phenyl organothiophosphate insecticides: azothoate, bromophos, bromophos-ethyl, carbophenothion, chlorthiophos, cyanophos, cythioate, dicapthon, dichlofenthion, etaphos, famphur, fenchlorphos, fenitrothion, fensulfothion, fenthion, fenthion-ethyl, heterophos, jodfenphos, mesulfenfos, parathion, parathion-methyl, phenkapton, phosnichlor, profenofos, prothiofos, sulprofos, temephos, trichlormetaphos-3, trifenofos
- phosphonate insecticides: butonate, trichlorfon
- phosphonothioate insecticides: mecarphon phenyl ethylphosphonothioate insecticides: fonofos, trichloronat phenyl phenylphosphonothioate insecticides: cyanofenphos, EPN, leptophos phosphoramidate insecticides: crufomate, fenamiphos, fosthietan, mephosfolan, phosfolan, pirimetaphos phosphoramidothioate insecticides: acephate, isocarbophos, isofenphos, isofenphos-methyl, methamidophos, propetamphos phosphorodiamide insecticides: dimefox, mazidox, mipafox, schradan oxadiazine insecticides: indoxacarb oxadiazolone insecticides: metoxadiazone phthalimide insecticides: dialifos, phosmet, tetramethrin pyrazole insecticides: chlorantraniliprole, cyantraniliprole, dimetilan, tebufenpyrad, tolfenpyrad phenylpyrazole insecticides: acetoprole, ethiprole, fipronil, pyraclofos, pyrafluprole, pyriprole, vaniliprole pyrethroid insecticides pyrethroid ester insecticides: acrinathrin, allethrin (bioallethrin), barthrin, bifenthrin, bioethanomethrin, cyclethrin, cycloprothrin, cyfluthrin (beta-cyfluthrin), cyhalothrin, (gamma-cyhalothrin, lambda-cyhalothrin), cypermethrin (alpha-cypermethrin, beta-cypermethrin, theta-cypermethrin, zeta-cypermethrin), cyphenothrin, deltamethrin, dimefluthrin, dimethrin, empenthrin, fenfluthrin, fenpirithrin, fenpropathrin, fenvalerate (esfenvalerate), flucythrinate, fluvalinate (tau-fluvalinate), furethrin, imiprothrin, metofluthrin, permethrin (biopermethrin, transpermethrin), phenothrin, prallethrin, profluthrin, pyresmethrin, resmethrin (bioresmethrin, cismethrin), tefluthrin, terallethrin, tetramethrin, tralomethrin, transfluthrin pyrethroid ether insecticides: etofenprox, flufenprox, halfenprox, protrifenbute, silafluofen pyrimidinamine insecticides: flufenerim, pyrimidifen pyrrole insecticides: chlorfenapyr tetramic acid insecticides: spirotetramat tetronic acid insecticides: spiromesifen thiazole insecticides: clothianidin, thiamethoxam thiazolidine insecticides: tazimcarb, thiacloprid thiourea insecticides: diafenthiuron urea insecticides: flucofuron, sulcofuron, see also chitin synthesis inhibitors unclassified insecticides: closantel, copper naphthenate, crotamiton, EXD, fenazaflor, fenoxacrim, hydramethylnon, isoprothiolane, malonoben, metaflumizone, nifluridide, plifenate, pyridaben, pyridalyl, pyrifluquinazon, rafoxanide, sulfoxaflor, triarathene, triazamate.

The foregoing insecticides, and links for a further identification and description of the insecticides, can be found at http://www.alanwood.net/pesticides/class_insecticides.html, which is incorporated herein in its entirety.

A particularly preferred herbicide is glyphosate (C3H8NO5P, [(phosphonomethyl)amino] acetic acid, CAS#1071-83-6). Other herbicides which can be used in the invention include:

amide herbicides: allidochlor, amicarbazone, beflubutamid, benzadox, benzipram, bromobutide, cafenstrole, CDEA, cyprazole, dimethenamid (dimethenamid-P), diphenamid, epronaz, etnipromid, fentrazamide, flucarbazone, flupoxam, fomesafen, halosafen, isocarbamid, isoxaben, napropamide, naptalam, pethoxamid, propyzamide, quinonamid, saflufenacil, tebutam anilide herbicides: chloranocryl, cisanilide, clomeprop, cypromid, diflufenican, etobenzanid, fenasulam, flufenacet, flufenican, ipfencarbazone, mefenacet, mefluidide, metamifop, monalide, naproanilide, pentanochlor, picolinafen, propanil, sulfentrazone arylalanine herbicides: benzoylprop, flamprop (flamprop-M), chloroacetanilide herbicides: acetochlor, alachlor, butachlor, butenachlor, delachlor, diethatyl, dimethachlor, metazachlor, metolachlor (S-metolachlor), pretilachlor, propachlor, propisochlor, prynachlor, terbuchlor, thenylchlor, xylachlor sulfonanilide herbicides: benzofluor, cloransulam, diclosulam, florasulam, flumetsulam, metosulam, perfluidone, pyrimisulfan, profluazol sulfonamide herbicides: asulam, carbasulam, fenasulam, oryzalin, penoxsulam, pyroxsulam, see also sulfonylurea herbicides thioamide herbicides: bencarbazone, chlorthiamid antibiotic herbicides: bilanafos aromatic acid herbicides:

benzoic acid herbicides: chloramben, dicamba, 2,3,6-TBA, tricamba pyrimidinyloxybenzoic acid herbicides: bispyribac, pyriminobac pyrimidinylthiobenzoic acid herbicides: pyrithiobac phthalic acid herbicides: chlorthal picolinic acid herbicides: aminopyralid, clopyralid, picloram quinolinecarboxylic acid herbicides: quinclorac, quinmerac arsenical herbicides: cacodylic acid, CMA, DSMA, hexaflurate, MAA, MAMA, MSMA, potassium arsenite, sodium arsenite benzoylcyclohexanedione herbicides: mesotrione, sulcotrione, tefuryltrione, tembotrione benzofuranyl alkylsulfonate herbicides: benfuresate, ethofumesate benzothiazole herbicides: benazolin, benzthiazuron, fenthiaprop, mefenacet, methabenzthiazuron carbamate herbicides: asulam, carboxazole, chlorprocarb, dichlormate, fenasulam, karbutilate, terbucarb carbanilate herbicides: barban, BCPC, carbasulam, carbetamide, CEPC, chlorbufam, chlorpropham, CPPC, desmedipham, phenisopham, phenmedipham, phenmediphamethyl, propham, swep cyclohexene oxime herbicides: alloxydim, butroxydim, clethodim, cloproxydim, cycloxydim, profoxydim, sethoxydim, tepraloxydim, tralkoxydim cyclopropylisoxazole herbicides: isoxachlortole, isoxaflutole dicarboximide herbicides: cinidon-ethyl, flumezin, flumiclorac, flumioxazin, flumipropyn, see also uracil herbicides dinitroaniline herbicides: benfluralin, butralin, dinitramine, ethalfluralin, fluchloralin, isopropalin, methalpropalin, nitralin, oryzalin, pendimethalin, prodiamine, profluralin, trifluralin dinitrophenol herbicides: dinofenate, dinoprop, dinosam, dinoseb, dinoterb, DNOC, etinofen, medinoterb diphenyl ether herbicides: ethoxyfen nitrophenyl ether herbicides: acifluorfen, aclonifen, bifenox, chlomethoxyfen, chlornitrofen, etnipromid, fluorodifen, fluoroglycofen, fluoronitrofen, fomesafen, furyloxyfen, halosafen, lactofen, nitrofen, nitrofluorfen, oxyfluorfen dithiocarbamate herbicides: dazomet, metam halogenated aliphatic herbicides: alorac, chloropon, dalapon, flupropanate, hexachloroacetone, iodomethane, methyl bromide, monochloroacetic acid, SMA, TCA imidazolinone herbicides: imazamethabenz, imazamox, imazapic, imazapyr, imazaquin, imazethapyr inorganic herbicides: ammonium sulfamate, borax, calcium chlorate, copper sulfate, ferrous sulfate, potassium azide, potassium cyanate, sodium azide, sodium chlorate, sulfuric acid nitrile herbicides: bromobonil, bromoxynil, chloroxynil, dichlobenil, iodobonil, ioxynil, pyraclonil organophosphorus herbicides: amiprofos-methyl, anilofos, bensulide, bilanafos, butamifos, 2,4-DEP, DMPA, EBEP, fosamine, glufosinate (glufosinate-P), glyphosate, piperophos oxadiazolone herbicides: dimefuron, methazole, oxadiargyl, oxadiazon oxazole herbicides: carboxazole, fenoxasulfone, isouron, isoxaben, isoxachlortole, isoxaflutole, monisouron, pyroxasulfone, topramezone phenoxy herbicides: bromofenoxim, clomeprop, 2,4-DEB, 2,4-DEP, difenopenten, disul, erbon, etnipromid, fenteracol, trifopsime
    phenoxyacetic herbicides: 4-CPA, 2,4-D, 3,4-DA, MCPA, MCPA-thioethyl, 2,4,5-T
    phenoxybutyric herbicides: 4-CPB, 2,4-DB, 3,4-DB, MCPB, 2,4,5-TB
    phenoxypropionic herbicides: cloprop, 4-CPP, dichlorprop (dichlorprop-P), 3,4-DP, fenoprop, mecoprop, (mecoprop-P)
        aryloxyphenoxypropionic herbicides: chlorazifop, clodinafop, clofop, cyhalofop, diclofop, fenoxaprop, (fenoxaprop-P), fenthiaprop, fluazifop, (fluazifop-P), haloxyfop, (haloxyfop-P), isoxapyrifop, metamifop, propaquizafop, quizalofop, (quizalofop-P), trifop phenylenediamine herbicides: dinitramine, prodiamine pyrazole herbicides: azimsulfuron, difenzoquat, halosulfuron, metazachlor, metazosulfuron, pyrazosulfuron, pyroxasulfone
    benzoylpyrazole herbicides: benzofenap, pyrasulfotole, pyrazolynate, pyrazoxyfen, topramezone
    phenylpyrazole herbicides: fluazolate, nipyraclofen, pinoxaden, pyraflufen pyridazine herbicides: credazine, pyridafol, pyridate pyridazinone herbicides: brompyrazon, chloridazon, dimidazon, flufenpyr, metflurazon, norflurazon, oxapyrazon, pydanon pyridine herbicides: aminopyralid, cliodinate, clopyralid, diflufenican, dithiopyr, flufenican, fluoroxypyr, haloxydine, picloram, picolinafen, pyriclor, pyroxsulam, thiazopyr, triclopyr pyrimidinediamine herbicides: iprymidam, tioclorim quaternary ammonium herbicides: cyperquat, diethamquat, difenzoquat, diquat, morfamquat, paraquat thiocarbamate herbicides: butylate, cycloate, di-allate, EPTC, esprocarb, ethiolate, isopolinate, methiobencarb, molinate, orbencarb, pebulate, prosulfocarb, pyributicarb, sulfallate, thiobencarb, tiocarbazil, tri-allate, vernolate thiocarbonate herbicides: dimexano, EXD, proxan thiourea herbicides: methiuron triazine herbicides: dipropetryn, indaziflam, triaziflam, trihydroxytriazine
    chlorotriazine herbicides: atrazine, chlorazine, cyanazine, cyprazine, eglinazine, ipazine, mesoprazine, procyazine, proglinazine, propazine, sebuthylazine, simazine, terbuthylazine, trietazine
    methoxytriazine herbicides: atraton, methometon, prometon, secbumeton, simeton, terbumeton
    methylthiotriazine herbicides: ametryn, aziprotryne, cyanatryn, desmetryn, dimethametryn, methoprotryne, prometryn, simetryn, terbutryn triazinone herbicides: ametridione, amibuzin, hexazinone, isomethiozin, metamitron, metribuzin triazole herbicides: amitrole, cafenstrole, epronaz, flupoxam triazolone herbicides: amicarbazone, bencarbazone, carfentrazone, flucarbazone, ipfencarbazone, propoxycarbazone, sulfentrazone, thiencarbazone triazolopyrimidine herbicides: cloransulam, diclosulam, florasulam, flumetsulam, metosulam, penoxsulam, pyroxsulam uracil herbicides: benzfendizone, bromacil, butafenacil, flupropacil, isocil, lenacil, saflufenacil, terbacil urea herbicides: benzthiazuron, cumyluron, cycluron, dichloralurea, diflufenzopyr, isonoruron, isouron, methabenzthiazuron, monisouron, noruron
    phenylurea herbicides: anisuron, buturon, chlorbromuron, chloreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluoron, phenobenzuron, siduron, tetrafluoron, thidiazuron
    sulfonylurea herbicides:
        pyrimidinylsulfonylurea herbicides: amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, metazosulfuron, nicosulfuron, orthosulfamuron, oxasulfuron, primisulfuron, propyrisulfuron, pyrazosulfuron, rimsulfuron, sulfometuron, sulfosulfuron, trifloxysulfuron
        triazinylsulfonylurea herbicides: chlorsulfuron, cinosulfuron, ethametsulfuron, iodosulfuron, metsulfuron, prosulfuron, thifensulfuron, triasulfuron, tribenuron, triflusulfuron, tritosulfuron
    thiadiazolylurea herbicides: buthiuron, ethidimuron, tebuthiuron, thiazafluoron, thidiazuron unclassified herbicides: acrolein, allyl alcohol, aminocyclopyrachlor, azafenidin, bentazone, benzobicyclon, bicyclopyrone, buthidazole, calcium cyanamide, cambendichlor, chlorfenac, chlorfenprop, chlorflurazole, chlorflurenol, cinmethylin, clomazone, CPMF, cresol, cyanamide, orthodichlorobenzene, dimepiperate, endothal, fluoromidine, fluridone, fluorochloridone, flurtamone, fluthiacet, indanofan, methyl isothiocyanate, OCH, oxaziclomefone, pentachlorophenol, pentoxazone, phenylmercury acetate, prosulfalin, pyribenzoxim, pyriftalid, quinoclamine, rhodethanil, sulglycapin, thidiazimin, tridiphane, trimeturon, tripropindan, tritac.

The foregoing herbicides, and links for a further identification and description of the herbicides, can be found at http://www.alanwood.net/pesticides/class_herbicides.html, which is incorporated herein in its entirety.

In many instances, pesticides having an amphoteric or positive surface charge are preferred. Such surface charge characteristics may be inherent in the pesticide employed, or may arise by applying an appropriate cationic or amphoteric surfactant onto the surfaces of pesticide particles. Generally, the surfactants are used at a level of from about 0.01-10% by weight (more preferably from about 0.1-3% by weight) based upon the total weight of the pesticide fraction in the overall composition taken as 100% by weight.

Suitable cationic surfactants include: dieicosyldimethyl ammonium chloride; didocosyldimethyl ammonium chloride; dioctadecyldimethyl ammonium chloride; dioctadecyldimethyl ammonium methosulphate; ditetradecyldimethyl ammonium chloride and naturally occurring mixtures of above fatty groups, e.g. di(hydrogenated tallow)dimethyl ammonium chloride; di(hydrogenated tallow)dimethyl ammonium metho-sulphate; ditallow dimethyl ammonium chloride; and dioleyidimethyl ammonium chloride.

These cationic surfactants also include imidazolinium compounds, for example, 1-methyl-1-(tallowylamido-)ethyl-2-tallowyl4,5-dihydroimidaz-olinium methosulphate and 1-methyl-1-(palmitoylamido)ethyl-2-octadecyl 4,5-dihydro-imidazolinium methosulphate. Other useful imidazolinium materials are 2-heptadecyl-1-methyl-1(2-stearoylamido)-ethyl-imidazoliniu-m methosulphate and 2-lauryl-lhydroxy-ethyl-1-oleyl-imidazolinium chloride.

Further examples of suitable cationic surfactants include: dialkyl(C12-C22)dimethylammonium chloride; alkyl(coconut)dimethylbenzylammonium chloride; octadecylamine acetate salt; tetradecylamine acetate salt; tallow alkylpropylenediamine acetate salt; octadecyltrimethylammonium chloride; alkyl(tallow)trimethylammonium chloride; dodecyltrimethylammonium chlorid; alkyl(coconut)trimethylammonium chloride; hexadecyltrimethylammonium chloride; biphenyltrimethylammonium chloride, alkyl(tallow)imidazoline quaternary salt; tetradecylmethylbenzylammonium chloride; octadecyldimethylbenzylammonium chloride; dioleyidimethylammonium chloride; polyoxyethylene dodecylmonomethylammonium chloride; polyoxyethylene alkyl (C12-C22)benzylammonium chloride; polyoxyethylene laurylmonomethyl ammonium chloride; 1-hydroxyethyl-2-alkyl(tallow)-imidazoline quaternary salt; and a silicone cationic surfactant having a siloxane group as a hydrophobic group, a fluorine-containing cationic surfactant having a fluoroalkyl group as a hydrophobic group.

Amphoteric (Zwitterionic) surfactants have a positive, negative, or both charges on the hydrophilic part of the molecule in acidic or alkaline media. Any suitable amphoteric surfactant may be used. For example, aminoproprionates may be employed where the alkyl chain of the aminoproprionate is preferably between about C.4 and about C.12 and may be branched or linear. The aminoproprionate may also be a sodium alkyl aminoproprionate. One representative commercially available product is sold under the trade name MIRATAINE JC-HA.

Other suitable amphoteric surfactants include, diproprionates such as Mirataine H2C-HA, sultaines such as Mirataine ASC, betaines such as Mirataine BET-O-30, amine oxides such as Barlox 12i and amphoteric imidazoline derivatives in the acetate form, Miranol JEM Conc, diproprionate form, Miranol C2M-SF Conc.), and sulfonates such as Miranol JS Conc.

Other examples of amphoteric surfactants include amino acid, betaine, sultaine, sulfobetaines, carboxylates and sulfonates of fatty acids, phosphobetaines, imidazolinium derivatives, soybean phospholipids, yolk lecithin, the alkali metal, alkaline earth metal, ammonium or substituted ammonium salts of alkyl amphocarboxy glycinates and alkyl amphocarboxypropionates, alkyl amphodipropionates, alkyl amphodiacetates, alkyl amphoglycinates and alkyl amphopropionates wherein alkyl represents an alkyl group having 6 to 20 carbon atoms, alkyliminopropionates, alkyl iminodipropionates and alkyl amphopropylsulfonates having between 12 and 18 carbon atoms, alkylbetaines and amidopropylbetaines and alkylsultaines and alkylamidopropylhydroxy sultaines wherein alkyl represents an alkyl group having 6 to 20 carbon atoms.

As indicated above, the copolymers of the invention contain respective quantities of maleic and itaconic moieties. These copolymers may exist in the acid form, as partial salts, or as saturated salts. When salts are employed, such can be formed using virtually any desired cationic species, particularly the akali metals and alkaline earth metals, e.g., the sodium, potassium, or calcium salts.

The copolymers of the invention are described in U.S. Pat. Nos. 6,515,090 and 6,706,837, both fully and completely incorporated by reference herein, with special reference to the operative examples of the '837 patent. In general, the copolymers should desirably contain from about 10-90% by weight maleic moieties (more preferably from about 25-75% by weight), and correspondingly from about 90-10% by weight itaconic moieties (more preferably from about 75-25% by weight). One particularly preferred copolymer of this class is commercialized by Specialty Fertilizer Products, LLC of Belton, Mo. under the trademark AVAIL®, which is a 40% by weight solids aqueous copolymer dispersion of substantially equimolar amounts of itaconic and maleic anhydride moieties partially neutralized with sodium ion (CAS# 556055-76-6) and having a pH of 6-8.

The amount of copolymer in the pesticide compositions of the invention can vary over wide limits, and the principal consideration is one of copolymer cost. Generally, the copolymer should be present at a level of from about 0.05-10% by weight (more preferably from about 0.1-4% by weight, and most preferably from about 0.2-2% by weight) based upon the total weight of the pesticide composition taken as 100% by weight.

The copolymer is preferably used in the form of a partial salt or a saturated salt. This is formed by the addition of a basic material such as sodium hydroxide or calcium hydroxide to achieve a pH in the range of from about 5-9, and more preferably from about 6-8. Lower pH acidic or partial salt copolymers can also be used, particularly with selected monomer ratios and pesticides. Generally, the pH should range from about 2-8.

The pesticide compositions of the invention, containing only a very minor amount of copolymer adjuvant, can be used at the same levels of use as the standard pesticide products without adjuvant. These levels vary between different pesticides, and the levels of use are well known in the art. However, owing to the synergistic effects of the copolymers, lesser usage levels may be appropriate.

The compositions and methods of the invention provide a greater pesticidal effectiveness as compared with the use of equal amount of the selected pesticide alone. Preferably, this increase should be at least about a three-fold greater effectiveness, and more preferably a four-fold increase in effectiveness.

The following examples set forth preferred compositions of the invention and pesticidal utilities thereof. It is to be understood, however, that these examples are provided by way of illustration and nothing therein should be taken as a limitation upon the overall scope of the invention.

EXAMPLE 1

In this example a series of commercially available insecticides were tested at various dilution levels and with and without a preferred copolymer, namely the AVAIL® copolymer previously described (a 40%-60% w/w aqueous composition of a saturated sodium salt of a maleic anhydride/itaconic acid copolymer in water). In each set of test runs, the selected insecticide was tested with a population of fire ants in order to determine the time required to kill the entire population. As explained above, the presence of the copolymer gave a distinct adjuvant effect and significantly increased the potency of the insecticides.

In particular, in each test run 20 ml of the respective liquid insecticide composition was added to a mason jar and swirled around the inside bottom thereof. The liquid was then poured off and the remainder was allowed to dry on the inner jar surface, creating substantially a monomeric dried layer. The outside neck surface of the jar was then coated in talc, and the open end of the jar was placed into a fire ant nest. The talc coating prevented the aggressive fire ants from climbing the outer surface of the jar. A population of fire ants was thus established in each jar, and the jar was then topped with an apertured mason jar cap. The time to death of all of the fire ants was then recorded.

In each case, the recommended concentration of insecticide was prepared (recorded as "1X"), followed by dilutions with water to create the diluted compositions. Where copolymer was used, the copolymer was added to the insecticide with gentle mixing, at a level of 30 ml per gallon. If desired, lesser amounts of copolymer could be used, e.g., 20 ml per gallon.

The following table sets forth the results of these tests.

TABLE 1

| INSECTICIDE COMPOSITION | | TIME TO DEATH (MIN) |
|---|---|---|
| malathion | 1X | 1 |
| malathion | 1/10X | 2 |
| malathion | 1/20X | 5 |
| malathion | 1/100X | 30 |
| malathion + AVAIL ® | 1/100X | 7 |
| permethrin | 1X | 5 |
| permethrin | 1/3X | 5 |
| permethrin | 1/10X | 5 |
| permethrin | 1/20X | 20 |
| permethrin + AVAIL ® | 1/20X | 2 |
| bifenthrin | 1/20X | 15 |
| bifenthrin + AVAIL ® | 1/20X | 5 |

The data of Table 1 clearly establishes the adjuvant effect of the copolymer with the tested insecticides. In all cases, the kill time for the lowest effective level of insecticide was materially lowered by the presence of the copolymer. Although the mechanism of this effect is not fully understood, it is believed that the tested insecticides, having an amphoteric or positive charge, are modified by the copolymer to change the membrane potential thereof, e.g., the copolymer aggregates the charge, rendering the insecticide/copolymer mixture more effective. This is confirmed by a series of tests with a negatively charged insecticide (Diazinon®) where the copolymer gave no decrease in kill times as compared with the insecticide itself.

EXAMPLE 2

In another series of tests, insecticides were tested with various copolymers having different ratios of maleic anhydride and itaconic acid moieties, and at different pH levels. In particular, respective copolymeric compositions were prepared made up of polymaleic acid, a 1:3 weight ratio of maleic anhydride to itaconic acid, a 1:1 weight ratio of maleic anhydride to itaconic acid, a 3:1 weight ratio of maleic anhydride to itaconic acid, and a 7:1 weight ratio of maleic anhydride to itaconic acid. Individual portions of each of these copolymers were then pH-modified using sodium hydroxide to provide, for each copolymer, portions with no pH adjustment, and with adjustment to pHs of 6, 7, and 8. These pH-modified test copolymers were then mixed with a 1/100× dilution of malathion at a level of 30 ml of copolymer per gallon of insecticide. Similarly, the same pH-adjusted copolymers were mixed with 1/20× water dilutions of permethrin, again at a level of 30 ml of copolymer per gallon of insecticide.

The test products were then used in the same fire ant kill experiment of Example 1, giving the data of Tables 2 and 3.

TABLE 2

| INSECTICIDE COMPOSITION | pH | TIME TO DEATH (MIN) |
|---|---|---|
| 1/100X malathion | — | 14 |
| Polymaleic Acid + 1/100X malathion | 6 | 9.5 |
| Polymaleic Acid + 1/100X malathion | 7 | 9 |
| Polymaleic Acid + 1/100X malathion | 8 | 8 |
| 1:3 Maleic Anhydride/Itaconic Acid Copolymer + 1/100X malathion | — | 8 |
| 1:3 Maleic Anhydride/Itaconic Acid Copolymer + 1/100X malathion | 6 | 7 |
| 1:3 Maleic Anhydride/Itaconic Acid Copolymer + 1/100X malathion | 7 | 5 |
| 1:3 Maleic Anhydride/Itaconic Acid Copolymer + 1/100X malathion | 8 | 8 |
| 1:1 Maleic Anhydride/Itaconic Acid Copolymer + 1/100X malathion | — | 12 |
| 1:1 Maleic Anhydride/Itaconic Acid Copolymer + 1/100X malathion | 6 | 8 |
| 1:1 Maleic Anhydride/Itaconic Acid Copolymer + 1/100X malathion | 7 | 8.5 |
| 1:1 Maleic Anhydride/Itaconic Acid Copolymer + 1/100X malathion | 8 | 8.5 |
| 3:1 Maleic Anhydride/Itaconic Acid Copolymer + 1/100X malathion | — | 7.5 |
| 3:1 Maleic Anhydride/Itaconic Acid Copolymer + 1/100X malathion | 6 | 6 |
| 3:1 Maleic Anhydride/Itaconic Acid Copolymer + 1/100X malathion | 7 | 7 |
| 3:1 Maleic Anhydride/Itaconic Acid Copolymer + 1/100X malathion | 8 | 5 |
| 7:1 Maleic Anhydride/Itaconic Acid Copolymer + 1/100X malathion | — | 9 |
| 7:1 Maleic Anhydride/Itaconic Acid Copolymer + 1/100X malathion | 6 | 4 |
| 7:1 Maleic Anhydride/Itaconic Acid Copolymer + 1/100X malathion | 7 | 6.5 |
| 7:1 Maleic Anhydride/Itaconic Acid Copolymer + 1/100X malathion | 8 | 6 |

TABLE 3

| INSECTICIDE COMPOSITION | pH | TIME TO DEATH (MIN) |
|---|---|---|
| Polymaleic Acid + 1/20X permethrin | — | Still Alive, 33 |
| Polymaleic Acid + 1/20X permethrin | 6 | 10 |
| Polymaleic Acid + 1/20X permethrin | 7 | 10.5 |
| Polymaleic Acid + 1/20X permethrin | 8 | 12 |
| 1:3 Maleic Anhydride/Itaconic Acid Copolymer + 1/20X permethrin | — | Still Alive, 27 |
| 1:3 Maleic Anhydride/Itaconic Acid Copolymer + 1/20X permethrin | 6 | 16 |
| 1:3 Maleic Anhydride/Itaconic Acid Copolymer + 1/20X permethrin | 7 | 15 |
| 1:3 Maleic Anhydride/Itaconic Acid Copolymer + 1/20X permethrin | 8 | 13 |
| 1:1 Maleic Anhydride/Itaconic Acid Copolymer + 1/20X permethrin | — | Still Alive, 37 |
| 1:1 Maleic Anhydride/Itaconic Acid Copolymer + 1/20X permethrin | 6 | 35 |
| 1:1 Maleic Anhydride/Itaconic Acid Copolymer + 1/20X permethrin | 7 | 19.5 |
| 1:1 Maleic Anhydride/Itaconic Acid Copolymer + 1/20X permethrin | 8 | 19 |
| 3:1 Maleic Anhydride/Itaconic Acid Copolymer + 1/20X permethrin | — | Still Alive, 32 |
| 3:1 Maleic Anhydride/Itaconic Acid Copolymer + 1/20X permethrin | 6 | 29 |
| 3:1 Maleic Anhydride/Itaconic Acid Copolymer + 1/20X permethrin | 7 | 27 |
| 3:1 Maleic Anhydride/Itaconic Acid Copolymer + 1/20X permethrin | 8 | 17 |
| 7:1 Maleic Anhydride/Itaconic Acid Copolymer + 1/20X permethrin | — | Still Alive, 20 |

TABLE 3-continued

| INSECTICIDE COMPOSITION | pH | TIME TO DEATH (MIN) |
|---|---|---|
| 1/20X permethrin | | |
| 7:1 Maleic Anhydride/Itaconic Acid Copolymer + 1/20X permethrin | 6 | 15 |
| 7:1 Maleic Anhydride/Itaconic Acid Copolymer + 1/20X permethrin + NaOH permethrin | 7 | 13 |
| 7:1 Maleic Anhydride/Itaconic Acid Copolymer + 1/20X permethrin | 8 | 13 |

The data of Tables 2 and 3 demonstrate that the preferred copolymers are useful over a wide range of different maleic anhydride/itaconic acid ratios, and that the copolymers are likewise effective over wide pH ranges.

EXAMPLE 3

In this example the effectiveness of the copolymers of the invention was tested with a glyphosate herbicide. An Iowa field having approximately 18-inch tall mixed bromegrass and orchard grass being prepared for corn planting was used as a test field. In order to plant, it was necessary to kill the weed grasses. It is known that an effective kill is very difficult using only one glyphosate application.

In the test, two quarts of standard commercial glyphosate was mixed with 40 gallons of 28% nitrogen liquid fertilizer made up of ⅓ urea by weight, ⅓ ammonium nitrate by weight, and ⅓ water by weight. As a comparison, two quarts of a 40% by weight solids maleic anhydride/itaconic acid copolymer (Nutrisphere® for liquids commercialized by Specialty Fertilizer Products, LLC, a calcium salt of maleic-itaconic copolymer, as a 30%-60% w/w solution in water, pH 1.5) was added to a separate quantity of the glyphosate-supplemented fertilizer.

Both test compositions were sprayed onto adjacent test plots of the field at a rate of 10 gallons per acre. After ten days, the plot sprayed with the glyphosate and copolymer-supplemented fertilizer exhibited essentially complete kill of the grasses. With the glyphosate-supplemented fertilizer without the copolymer, a second glyphosate spray application was required for a complete kill.

Thus, the copolymer of the invention allowed planting at an earlier time with reduced glyphosate consumption.

I claim:

1. A pesticide composition comprising respective quantities of a pesticide and a copolymer consisting of individual quantities of maleic and itaconic moieties, wherein said quantities total at least 93% by weight of itaconic and maleic moieties.

2. The pesticide composition of claim 1, said pesticide selected from the group consisting of insecticides and herbicides and mixtures thereof.

3. The pesticide composition of claim 1, said composition having at least about a two-fold greater pesticidal effectiveness, as compared with an equal amount of the pesticide without the copolymer.

4. The pesticide composition of claim 1, said copolymer being a copolymer containing from about 10-90% by weight maleic moieties, and from about 90-10% by weight itaconic moieties.

5. The pesticide composition of claim 1, said copolymer being present of from about 0.05-10% by weight, based upon the total weight of the composition taken as 100% by weight.

6. The pesticide composition of claim 5, said level being from about 0.2-2% by weight.

7. The pesticide composition of claim 1, said composition being an aqueous composition and having a pH of from about 5-9.

8. The pesticide composition of claim 1, said pesticide being glyphosate.

9. A method of pesticidal treatment comprising the step of applying a pesticide composition to a surface, said composition comprising respective quantities of a pesticide and a copolymer consisting of individual quantities of maleic and itaconic moieties, wherein said quantities total at least 93% by weight of itaconic and maleic moieties.

10. The method of claim 9, said pesticide selected from the group consisting of insecticides and herbicides and mixtures thereof.

11. The method of claim 9, said composition having at least about a two-fold greater pesticidal effectiveness, as compared with an equal amount of the pesticide without the copolymer.

12. The method of claim 9, said copolymer being a copolymer containing from about 10-90% by weight maleic moieties, and from about 90-10% by weight itaconic moieties.

13. The method of claim 9, said copolymer being present of from about 0.05-10% by weight, based upon the total weight of the composition taken as 100% by weight.

14. The method of claim 13, said level being from about 0.2-2% by weight.

15. The method of claim 9, said composition being an aqueous composition and having a pH of from about 5-9.

16. The method of claim 9, said pesticide being glyphosate.

17. The pesticide composition of claim 1, said copolymer being essentially free of any moieties other than said maleic and itaconic moieties.

18. The method of claim 9, said copolymer being essentially free of any moieties other than said maleic and itaconic moieties.

* * * * *

UNITED STATES PATENT AND TRADEMARK OFFICE
CERTIFICATE OF CORRECTION

PATENT NO. : 7,655,597 B1
APPLICATION NO. : 12/534481
DATED : February 2, 2010
INVENTOR(S) : John Larry Sanders Page 1 of 1

It is certified that error appears in the above-identified patent and that said Letters Patent is hereby corrected as shown below:

Column 13, line 47, cancel the text beginning with "1. A pesticide composition comprising" to and ending "maleic moieties." in column 13, line 51, and insert the following claim:

--1. A pesticide composition comprising respective quantities of a pesticide and a copolymer, wherein the copolymer consists of at least 93% by weight quantities of maleic and itaconic moieties.--

Column 14, line 22, cancel the text beginning with "9. A method of pesticidal treatment comprising" to and ending "maleic moieties." in column 14, line 27, and insert the following claim:

--9. A method of pesticidal treatment comprising the step of applying a pesticide composition to a surface, said composition comprising respective quantities of a pesticide and a copolymer, wherein the copolymer consists of at least 93% by weight quantities of maleic and itaconic moieties.--

Signed and Sealed this

Sixteenth Day of November, 2010

David J. Kappos
*Director of the United States Patent and Trademark Office*